United States Patent
Shen et al.

(10) Patent No.: US 9,186,356 B2
(45) Date of Patent: Nov. 17, 2015

(54) METHODS FOR TREATING FRONTOTEMPORAL LOBAR DEGENERATION WITH UBIQUITINATED INCLUSIONS (FTLD-U)

(75) Inventors: Che-Kun James Shen, Taipei (TW); Kuen-Jer Tsai, Kaosiung (TW)

(73) Assignee: Academia Sinica, Taipei (TW)

( * ) Notice: Subject to any disclaimer, the term of this patent is extended or adjusted under 35 U.S.C. 154(b) by 101 days.

(21) Appl. No.: 13/343,686

(22) Filed: Jan. 4, 2012

(65) Prior Publication Data

US 2012/0178775 A1 Jul. 12, 2012

Related U.S. Application Data

(60) Provisional application No. 61/430,970, filed on Jan. 8, 2011.

(51) Int. Cl.
| | |
|---|---|
| A61K 31/4436 | (2006.01) |
| A61K 31/132 | (2006.01) |
| A61K 31/138 | (2006.01) |
| A61K 31/513 | (2006.01) |
| A61K 31/55 | (2006.01) |
| A61K 31/7016 | (2006.01) |
| A61K 31/4433 | (2006.01) |

(52) U.S. Cl.
CPC ........... *A61K 31/4433* (2013.01); *A61K 31/132* (2013.01); *A61K 31/138* (2013.01); *A61K 31/513* (2013.01); *A61K 31/55* (2013.01); *A61K 31/7016* (2013.01)

(58) Field of Classification Search
CPC . A61K 31/436; A61K 31/132; A61K 31/138; A61K 31/513; A61K 31/55; A61K 31/7016
USPC ........................................................ 514/291
See application file for complete search history.

(56) References Cited

U.S. PATENT DOCUMENTS

2012/0064143 A1* 3/2012 Sharp et al. ................... 424/439

OTHER PUBLICATIONS

Zhang et al. "Rapamycin treatment augments motor neuron degeneration in SOD1G93A mouse model of amyotrophic lateral sclerosis" Autophagy 7:4, 1-14; Apr. 2011.
Kuen-Jer Tsai et al. "Elevated expression of TDP-43 in the forebrain of mice is sufficient to cause neurological and pathological phenotypes mimicking FTLD-U" J. Exp Med. vol. 207 No. 8 1661-1673.
Brinda Ravikumar et al. "Rapamycin pre-treatment protects against apoptosis" Human Molecular Genetics, 2006, vol. 15, No. 7 1209-1216.
Antonella Caccamo et al. "Rapamycin Rescues TDP-43 Mislocalization and the Associated Low Molecular Mass Neurofilament Instability" The Journal of Biological Chemistry vol. 284, No. 40, pp. 27416-27424, Oct. 2, 2009.
Brady OA, Meng P, Zheng Y, Mao Y, Hu F. "Regulation of TDP-43 aggregation by phosphorylation and p62/SQSTM1" J. Neurochem. (2011) 116, 248-259.
S Sarkar, B Ravikumar, RA Floto and DC Rubinsztein "Rapamycin and mTOR-independent autophagy inducers ameliorate toxicity of polyglutamineexpanded huntingtin and related proteinopathies" Cell Death and Differentiation (2009) 16, 46-56.

* cited by examiner

*Primary Examiner* — Sreeni Padmanabhan
*Assistant Examiner* — Sahar Javanmard
(74) *Attorney, Agent, or Firm* — Hsiu-Ming Saunders; Intellectual Property Connections, Inc.

(57) ABSTRACT

Methods for rescuing learning, memory and/or motor function deficits associated with frontotemporal lobar degeneration with ubiquitinated inclusions (FTLD-U) are disclosed. The method comprises: a) administering to an animal having FTLD-U a therapeutically effective amount of an autophagy inducer; b) causing a decrease in the amount of ubiquitinated TDP-43 aggregation forms in the brain of the animal; and c) causing an improvement of the learning, memory capacities and/or motor function of the animal.

7 Claims, 9 Drawing Sheets

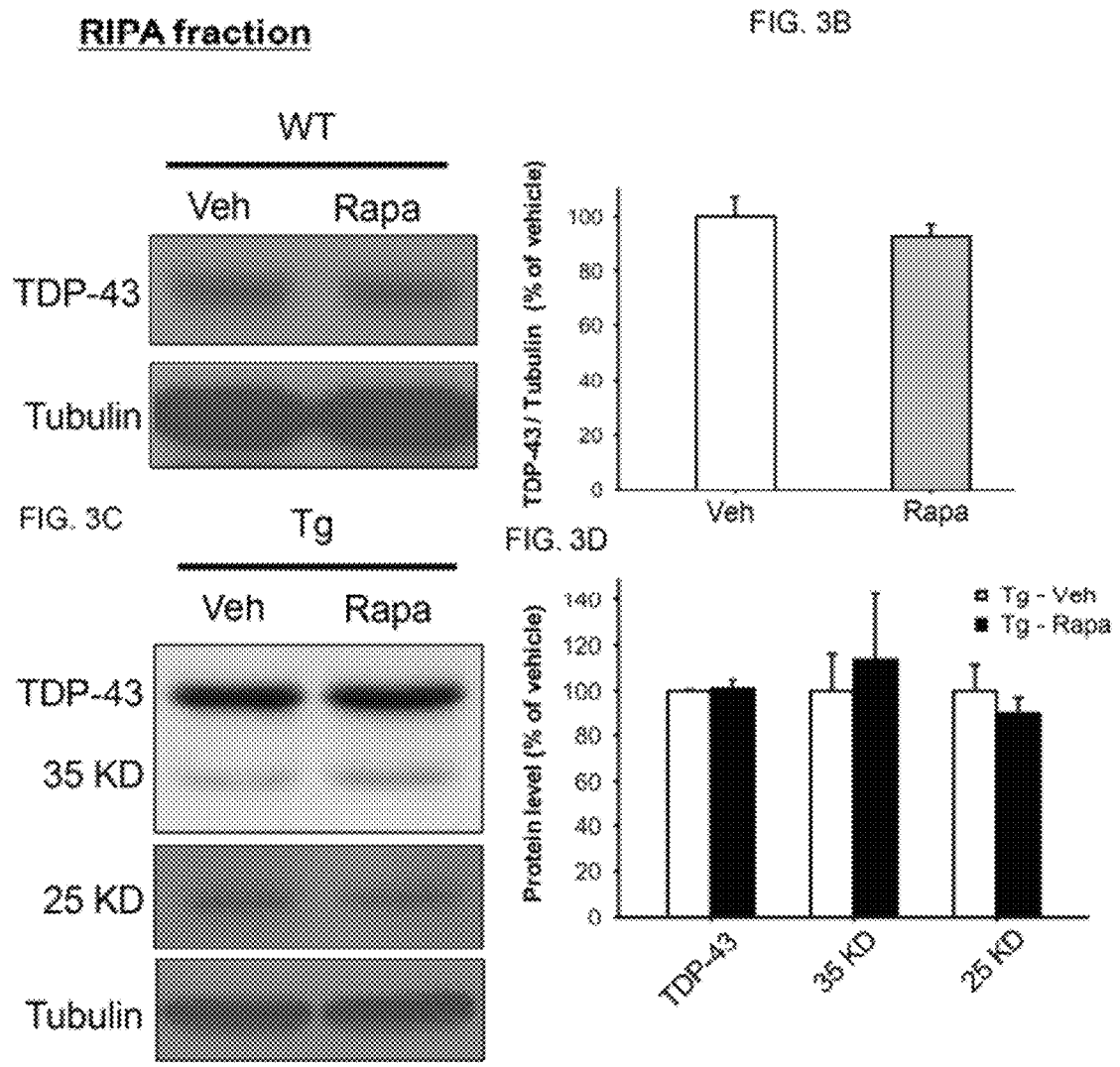

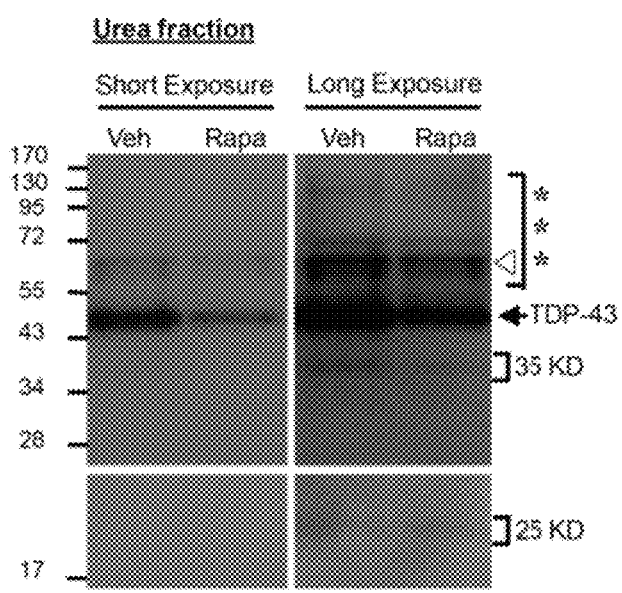
FIG. 3E
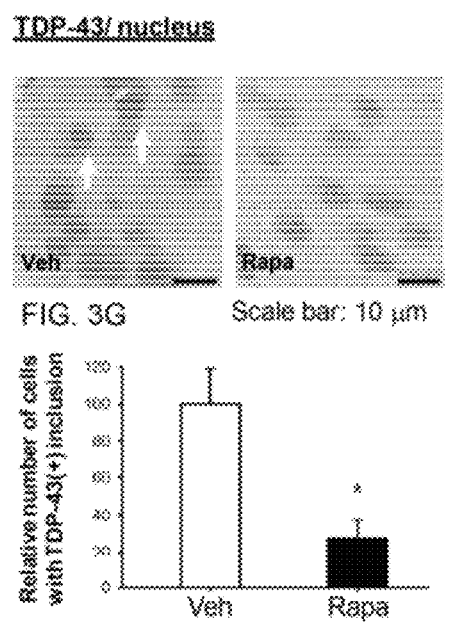
FIG. 3F
FIG. 3G

Tg vs SPD : P=0.004
Tg vs CBZ : P=0.049
Tg vs Tax : P=0.00016

METHODS FOR TREATING FRONTOTEMPORAL LOBAR DEGENERATION WITH UBIQUITINATED INCLUSIONS (FTLD-U)

REFERENCE TO RELATED APPLICATION

The present application claims the priority to U.S. Provisional Application Ser. No. 61/430,970, filed Jan. 8, 2011, which is herein incorporated by reference in its entirety.

FIELD OF THE INVENTION

The present invention relates generally to methods for treating frontotemporal lobar degeneration with ubiquitination (FTLD-U) disease, and more specifically to rescue of cognitive impairment and prevention of motor function deficiency in FTLD-U patients.

BACKGROUND OF THE INVENTION

TDP-43 is a 43 KD, ubiquitously expressed protein well conserved among the eukaryotes. This DNA/RNA-binding factor is predominantly located in the nucleus as a dimer, and it has been implicated to play roles in multiple cellular functions, e.g. transcriptional repression, splicing, and translation. TDP-43 has also been identified as the pathological signature protein of a range of neurodegenerative diseases. The pathological samples of these diseases, which have been termed TDP-43 proteinopathies, are characterized with cytoplasmic and, to a much less extent, nuclear TDP-43-positive (+) and ubiquitinated inclusions (UBIs) containing full-length TDP-43, poly-ubiquinated TDP-43, phosphorylated TDP-43, as well as 35 KD- and 25 KD carboxyl fragments of TDP-43. Of the two major categories of TDP-43 proteinopathies are frontotemporal lobar degeneration with ubiquitin (+) inclusions (FTLD-U) and amyotrophic lateral sclerosis (ALS). It has been estimated that approximately 50% of FTLD-U and 80-90% of ALS, which has an incidence rate between 1.5 and 2.5 per 100,000, are signified with TDP-43 (+) UBIs (6). Furthermore, numerous experimental data have suggested that mis-regulation of the metabolism of TDP-43, including the formation of the TDP-43 (+) UBIs, plays a causative role in the pathogenesis. Thus, it would be logical to identify the potential drugs of FTLD-U and ALS with TDP-43 proteinopathies, for which there is no effective drug therapy yet, by targeting either TDP-43 or the TDP-43 (+) inclusions.

Caccamo et al. (2009) overexpressed ~25 kDa C-terminal fragment (the last 199 amino acids; C199-TDP) of TDP-43 in N2A mouse and SH-SYSY human neuroblastoma cell lines, leading to a redistribution/mislocalization of endogenous TDP-43 from nucleus to the cytoplasm. They reported that rapamycin treatment reduced the steady-state levels of ~25 kDa fragment, decreased the mislocalization of TDP-43 to cytoplasm, but rapamycin had no effect on the amount of full-length TDP-43 in the C199-TDP transfected cells (JOURNAL OF BIOLOGICAL CHEMISTRY VOL. 284, NO. 40, pp. 27416-27424). The C199-TDP transfected neuroblastoma cell line does not mimic the FTLD-U disease, nor displays symptoms of FTLD-U. It is not a scientifically recognized animal model for FTLD-U disease. Furthermore, patients with FTLD-U have type 3 ubiquitin-positive, TDP-43 positive, tau-negative pathology at post-mortem. Cytosolic TDP-43 (+) inclusions in patients with FTLD-U contain not only ~25 kDa but also ubiquinated TDP-43, full-length TDP-43 and ~35 kDa fragments. Clinical symptoms of FTLD are complex and progress with the stage of the disease. There are three clinical subtypes for FTLD: behavioural-variant frontotemporal dementia, semantic dementia and progressive nonfluent aphasia. The symptoms of frontotemporal dementia (FTD) can be classified roughly into two groups which underlie the functions of the frontal lobe: behavioural symptoms (and/or personality change) and symptoms related to problems with executive function. Semantic dementia (SD) is a progressive neurodegenerative disorder characterized by loss of semantic memory in both the verbal and non-verbal domains. The major symptom of progressive nonfluent aphasiais progressive difficulties with the production of speech. It is not known whether autophage enhancers would improve any clinical symptoms of patients with FTLD-U.

Moreover, there are contradicting reports about the relationship of autophage and cell death. Ravikumar et al. (2006) reported that rapamycin pretreatment reduced mitochondrial loads and protected against apoptosis including neuronal death (*Human Molecular Genetics*, Vol. 15, No. 7 1209-1216). However, Zhang et al. (2011) reported that treatment with autophage enhancer rapamycin caused more server mitochondria impairment, accelerated motor neuron degeneration, shortened the life span of the amyotrophic lateral sclerosis (ALS) mice, and had no obvious effects on the accumulation of in copper-zinc superoxide dismutase (SOD1) aggregates, suggesting that rapamycin treatment may exacerbate the pathological processing through apoptosis and other mechanisms in the ALS mice "Rapamycin treatment augments motor neuron degeneration in SOD1G93A mouse model of amyotrophic lateral sclerosis" *Autophagy* 7:4, 1-14).

A previously unaddressed need exists in the art to address the aforementioned deficiencies and inadequacies, especially in connection with an effective drug for FTLD-U.

SUMMARY OF THE INVENTION

In one aspect, the invention relates to a method of rescuing learning, memory and/or motor function deficits associated with frontotemporal lobar degeneration with ubiquitinated inclusions (FTLD-U), comprising: a) administering to an animal having FTLD-U a therapeutically effective amount of rapamycin or a derivative thereof; b) causing a decrease in the amount of ubiquitinated TAR DNA-binding protein of 43 kDa (TDP-43); and c) causing an improvement of the learning, memory capacities and/or motor function of the animal.

In another aspect, the invention relates to a method of preventing the presence of ubiquitinated TDP-43, comprising: a) administering to an animal in need thereof a therapeutically effective amount of rapamycin or a derivative thereof; and b) decreasing the amount of ubiquitinated TDP-43 in the brain of the animal.

Further in another aspect, the invention relates to a method of rescuing learning, memory and/or motor function deficits associated with frontotemporal lobar degeneration with ubiquitinated inclusions (FTLD-U), comprising: a) administering to an animal having FTLD-U a therapeutically effective amount of an autophagy inducer; b) causing a decrease in the amount of ubiquitinated TDP-43 aggregation forms in the brain of the animal; and c) causing an improvement of the learning, memory capacities and/or motor function of the animal.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 3A-G show rampacin effects on the solubility and subcellular distribution of TDP-43 in FTLD-U mouse brains. (3A-D) Western blot analysis of TDP-43 in the soluble/RIPA fractions of extracts from the cortex and hippocampus regions of 6 month-old WT (3A-B) and TDP-43 Tg mice (3C-D) treated with rapamycin or vehicle. The RIPA fractions of the extracts were prepared as described in Materials and Methods and analyzed by Western blotting. Note that rapamycin and vehicle treatments resulted in similar levels of the different TDP-43 species in either the WT or the Tg mouse samples. The amounts of the 35 KD and 25 KD TDP-43 fragments in the WT extract were too low to be analyzed. (3E) Western blot analysis of TDP-43 in the urea-soluble fractions of the brain extracts. The arrow points to the unmodified form of TDP-43 on the gel. The triangle is an anti-TDP-43 hybridizing band of unknown origin. *** represents the gel region containing high molecular weight, poly-ubiquitinated TDP-43 species. (3F) lmmunohistochemical staining of TDP-43 and nuclei of brain sections from TDP-43 Tg mice treated with rapamycin or vehicle. The sections were immunohistochemically stained for detection of TDP-43 (brown) and nuclei (blue) as described in the Materials and Methods. The TDP-43 (+) inclusions are indicated by the white arrows. Bars, 10 μm. (3G) The quantitative analysis of the relative numbers of TDP-43 (+) inclusions is shown in the histogram below the photo panels.

DETAILED DESCRIPTION OF THE INVENTION

Definitions

Figure 1:
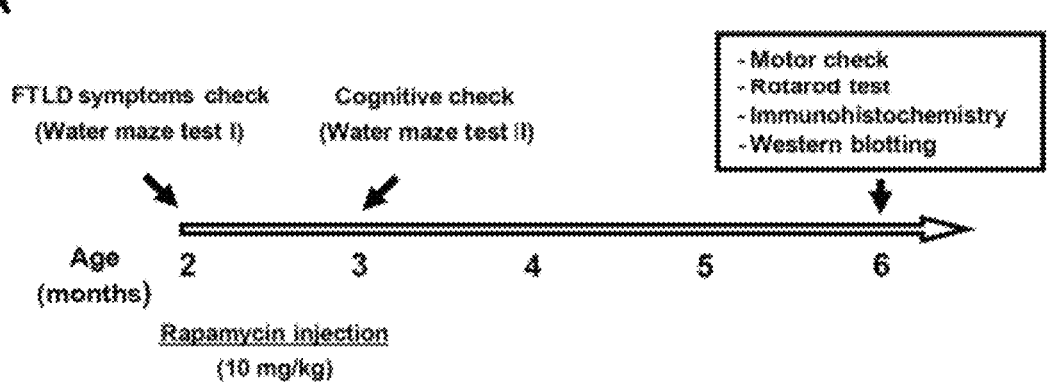
FIGS. 1A-C show the results of phenotype characterizations of rapamycin-treated FTLD-U mice. (A) Flow chart of the rapamycin treatment of the mice. The WT and TDP-43 Tg mice were treated with the vehicle or rapamycin as described in the Materials and Methods. The treatment continued from the age of 2 months to the age of 6 months. Water maze tests (I and II) were carried out at the ages of 2 months and 3 months, respectively, and the rotarod test was carried out at the age of 6 months. (B) Water maze performances of 3 months-old WT and TDP-43 Tg mice after treatment with rapamycin or vehicle for 1 month. Note the rescued performance of the Tg mice after treatment with rapamycin (Tg-Rapa) in comparison to the ones treated with vehicle (Tg-Veh). (C) Rotarod performances of 6 month old WT and TDP-43 Tg mice after treatment with rapamycin or vehicle for 4 months. Note the better performance of the Tg-Rapa mice than the Tg-veh mice.
Figure 1:
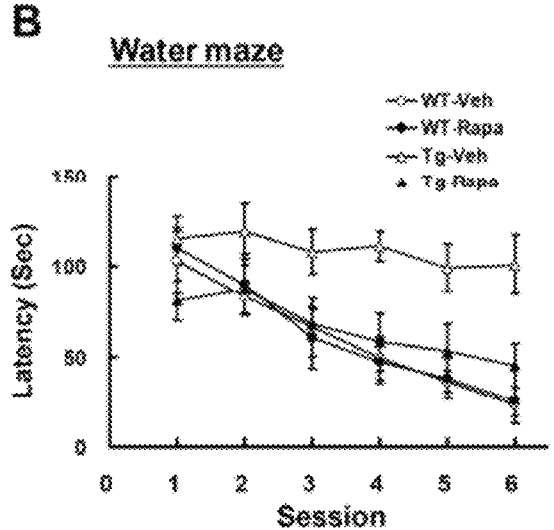
Figure 1:
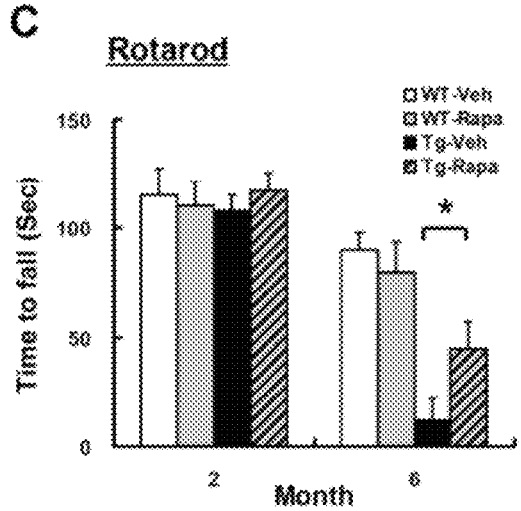

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" refers to administering an effective amount a drug to a subject that has FTLD, or has a symptom of FTLD, or has a predisposition toward such a disorder, with the purpose to cure, heal, alleviate, relieve, alter, remedy, ameliorate, improve, or affect the disorder, the symptoms of the disorder, or the predisposition toward the disorder. The term "treating", "treat" or "treatment" as used herein includes preventative (e.g., prophylactic) and palliative treatment.

An "effective amount" refers to a dose of the composition that is sufficient to provide a therapeutic benefit.

As used herein, "autophagy" or "autophagocytosis" shall generally mean a catabolic process involving the degradation of a cell's own components through the lysosomal machinery. An autophagy inducer includes, but not limited to, rapamycin, tamoxifen, carbamazepine, calpastatin, and minoxidil.

The term "insoluble full-length TDP-43 and ~35 kDa fragment" shall generally refers to full-length TDP-43 and ~35 kDa fragment inclusions, which are not water soluble but are soluble in urea.

The term "ubiquitinated TDP-43" shall generally refer to ubiquitinated TAR DNA-binding protein of 43 kDa inclusions.

The terms "ubiquitinated TDP-43 aggregates" and "ubiquitinated TDP-43 inclusions" are interchangeable.

The term "frontotemporal lobar degeneration with ubiquitinated inclusions (FTLD-U)" shall generally mean the pathology that is mostly commonly associated with frontotemporal dementia (FTD) characterized by the presence of neuronal inclusions in the neocortex and hippocampal dentate granule cells that are immunoreactive for ubiquitin (ub-ir) but negative for tau and α-synuclein.

Proteinopathy shall generally mean any disease (especially a neurodegenerative disease) caused by a malformed protein. Proteinopathies are a family of human disease caused by toxic aggregation-prone proteins and featured by the presence of protein aggregates in the affected cells.

The Morris water navigation task is a behavioral procedure widely used in behavioral neuroscience to study spatial learning and memory.

The Rotarod Performance test is a performance test based on a rotating rod with forced motor activity being applied, usually by a rodent. The Rotarod Performance test measures parameters such as riding time (seconds) or endurance. Some of the functions of the Rotarod Performance test include evaluating balance and coordination of the subjects; especially in testing the effect of experimental drugs.

TDP-43 is a multi-functional DNA/RNA-binding protein that has been identified as the major component of the cytoplasmic ubiquitin (+) inclusions (UBIs) in the diseased cells of frontotemporal lobar dementia (FTLD-U) and amyotrophic lateral sclerosis (ALS). Unfortunately, effective drugs for these neurodegenerative diseases are yet to be developed.

The invention relates to the therapeutic potential of rapamycin, an m-TOR inhibitor, in an animal with ubiquitinated TDP-43 inclusions. Here it was shown that rapamycin treatment effectively rescued the learning/memory impairment of FTLD-U mice at 2 months of age, and it significantly prevented the age-dependent loss of their motor function. These behavioral improvements upon rapamycin treatment were accompanied with decreased level of caspase-3, and a reduction of neuron loss in the forebrain of the FTLD-U mice. Furthermore, the number of cells with cytosolic TDP-43 (+) inclusions and the amounts of full-length TDP-43 as well as its cleavage products (35 KD and 25 KD) in the urea-soluble fraction of the cellular extract were significantly decreased upon rapamycin treatment. These changes of the TDP-43 metabolism were accompanied with rapamycin-induced decreases of the mTOR regulated P-p70 and the p62 protein, as well as increases of the autophagic marker LC3. The data suggest that rapamycin is a potentially useful drug for the therapy of neurodegenerative diseases with ubiquitinated TDP-43 inclusions, and it acts in part through clearance of the TDP-43 (+) UBIs via its known autophagy-enhancing property.

In one aspect, the invention relates to a method of rescuing learning, memory and/or motor function deficits associated with frontotemporal lobar degeneration with ubiquitinated inclusions (FTLD-U), comprising: a) administering to an animal with FTLD-U a therapeutically effective amount of rapamycin or a derivative thereof; b) causing a decrease in the amount of TAR DNA-binding protein of 43 kDa (TDP-43) positive (+) ubiquitinated inclusions in the brain of the animal; and c) causing an improvement of the learning, memory capacities and/or motor function of the animal.

In one embodiment of the invention, the aforementioned method further comprises: d) assessing the learning and/or memory capacities of the animal; and/or e) evaluating the motor coordination and/or balance of the animal.

In another embodiment of the invention, the animal has an early stage of frontotemporal lobar degeneration with ubiquitinated inclusions (FTLD-U).

In another embodiment of the invention, the aforementioned method further comprises causing a prevention of a loss of motor neuron function in the animal.

In another embodiment of the invention, the aforementioned method further comprises causing a dissociation and/or dissolution of TDP-43 (+) inclusions in the brain of the animal as compared without treatment; and/or causing a decrease in the amount of ubiquitinated TDP-43, insoluble full-length TDP-43 and ~35 kDa fragments in the brain of the animal as compared without treatment. Furthermore, the aforementioned method does not cause a decrease in the amount of soluble full-length TDP-43, ~35 kDa and ~25 kDa fragments in the brain of the animal.

In another embodiment of the invention, rapamycin or a derivative thereof is administered via injection at a regimen of ≥10 mg/kg for a period of at least 1 month. It is critical to administer to the animal with FTLD-U a sufficient dose of rapamycin to achieve a desired pharmacological effect.

In another aspect, the invention relates to a method of preventing the presence of ubiquitinated TDP-43, comprising: a) administering to an animal in need thereof a therapeutically effective amount of rapamycin or a derivative thereof; and b) decreasing the amount of TDP-43 (+) ubiquitinated inclusions in the brain of the animal.

In one embodiment of the invention, the animal suffers from learning, memory and/or motor function deficits.

In another embodiment of the invention, the aforementioned method further comprises causing a prevention of a neuronal loss in the brain of the animal.

In another embodiment of the invention, the aforementioned method further comprises causing a dissociation and/or dissolution of TDP-43 (+) inclusions and/or causing a decrease in the amount of ubiquitinated TDP-43, insoluble full-length TDP-43 and ~35 kDa fragments without decreasing the amount of soluble full-length TDP-43, ~35 kDa and ~25 kDa fragments in the brain of the animal.

Further in another aspect, the invention relates to a method of rescuing learning, memory and/or motor function deficits associated with frontotemporal lobar degeneration with ubiquitinated inclusions (FTLD-U), comprising: a) administering to an animal with FTLD-U a therapeutically effective amount of an autophagy inducer; b) causing a decrease in the amount of TDP-43 (+) ubiquitinated inclusions in the brain of the animal; and c) causing an improvement of the learning, memory capacities and/or motor function of the animal.

In one embodiment of the invention, the aforementioned step c) comprises causing an improvement of motor function of the animal.

In another embodiment of the invention, the aforementioned method further comprises causing a decrease in the number of neurons with TDP-43 (+) inclusions in the brain of the animal.

In another embodiment of the invention, the autophagy inducer is at least one chosen from rapamycin, tamoxifen, carbamazepine, calpastatin, minoxidil, spermidine, and trehalose.

Further in another embodiment of the invention, the autophagy inducer comprises tamoxifen, carbamazepine or spermidine.

Yet in another embodiment of the invention, the method further comprises causing a prevention of a neuronal loss in the brain of the animal.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
FTLD-U Mouse Model

The FTLD-U mouse model carried transgenic full-length mouse TDP-43 cDNA under the transcription control of a 8.5 kb promoter region of the Ca2+/calmodulin-dependent kinase II, CaMKII, gene (K. J. Tsai et al. (2010) "Elevated expression of TDP-43 in the forebrain of mice is sufficient to cause neurological and pathological phenotypes mimicking FTLD-U" *J. Exp. Med.* 207, 1661, which is incorporparated herein by reference by its entirety). Genotyping by PCR and Southern blotting were used to identify the transgene-positive mice of the founders and their progenies, and Western blotting and immunohistochemistry were used to check the expression of the transgene in specific regions, in particular the hippocampus and cortex. The assays of the behavioral performances and pathological features of the homozygous (+/+) TDP-43 Tg mice were done as described before. The mice were bred at the Animal Facility of the Institute of Molecular Biology (IMB), Academia Sinica, Taiwan. Experimental procedures for handling the mice followed the Guidelines of IMB. The animals were housed in a room maintained on a 12-h/12-h light/dark cycle (light on at 7:00 a.m.).

Drug Treatment

Rapamycin powder (Sirolimus, LC Laboratories) was dissolved in ethanol and stored at −20° C. in aliquots of the concentration of 25 mg/ml. The working solution was prepared freshly before use with a final concentration of 1 mg/ml rapamycin in 2% ethanol. For the Morris water maze tests, the WT and TDP-43 Tg (+/+) mice of the age 2 months were injected intraperitoneally with rapamycin (10 mg/kg) three times a week for a period of 4 months. The control animals were injected with PBS (vehicle) in parallel. Water maze tests were carried out first at the age of 2 months to ascertain the impairment of the learning/memory of the Tg mice, and then at the age of 3 months to examine the effect of rapamycin on the cognition. The rotarod tests were carried out at the age of 6 months.

Other autophage inducers for administration to the FTLD-U mice include tamoxifen, carbamazepine, calpastatin, minoxidial, spermidine and trehalose. Tamoxifen can inhibit PKB and increase beclin 1. Carbamazepine can lower inositol and $IP_3$ levels. Calpastatin is a calpain inhibitor. Minoxidial is a $K^+_{ATP}$ channel opener. Spermidine can decrease ROS and increases beclin 1. The effect of trehalose is unknown. Tamoxifen (80 mg/Kg) was administered via subcutaneous injection, once per day for one week. carbamazepine (50 mg/Kg) was administered i.p. once per day for two weeks. Spermidine (50 mg/Kg) was administered i.p. once per day for one week.

Morris Water Maze Task

For assessment of spatial learning, the Morris water maze task was used as described previously (K. J. Tsai, Y. C. Tsai, C. K. Shen (2007) "G-CSF rescues the memory impairment of animal models of Alzheimer's disease" *J. Exp. Med.* 204, 1273). The animals were subjected to four trials per session and two sessions a day. A complete test consisted of 6 sessions in 3 days. The average time spent by the individual mice to reach the platform in the water was recorded as the escape latency.

Rota Rod Test

The rotarod tests were performed as described before (K. J. Tsai el al. (2010) *J. Exp. Med.* 207, 1661). In brief, the mice were placed on a rod rotating at 20 r.p.m. and the time taken for them to fall from the rod was measured. If a mouse stayed on the rod until the end of the 2 min trial, a time of 120 sec was recorded.

Immunohistochemistry

The immunohistochemistry analysis of the adult brains was performed as described previously (K. J. Tsai et al. (2010) *J. Exp. Med.* 207, 1661). For immunohistostaining, the brain sections were stained with anti-TDP-43 (Gene Tex, Inc.), anti-caspase-3 (Cell signaling) or anti-NeuN (Millipore), and then with the biotin-conjugated secondary antibodies (Millipore) followed by detection with DAB (Millipore). Hematoxylain was used to locate the nuclei.

For immunofluorescence staining, the coronal sections were stained with the anti-LC3 antibody (Novus Biologicals). DAPI staining was used to locate the nuclei. All sections were examined in a laser scanning confocal microscope (LSM 510, Carl Zeiss Inc.).

Western Blotting Analysis of Brain Extracts

For analysis of the expression levels of different proteins, the extracts were prepared from the hippocampus and cortex of the cerebrum of the male WT and TDP-43 Tg mice of the age 6-month. For analysis of the soluble proteins, the tissues were homogenized in RIPA lysis buffer (50 mM Tris-HCl, 150 mM NaCl, 1% Igepal CA-630, 2 mM EDTA, pH 8.0, 1 mM $Na_3VO_4$, 20 μg/ml pepstatin A, 20 μg/ml leupeptin, 20 μg/ml aprotinin, 1 mM PMSF, 50 mM NaF). The extracts were then analyzed by Western blotting with use of anti-TDP-43 (Gene Tex), anti-caspase-3 (Cell Signaling), anti-LC3 (Novus Biologicals), anti-phospho-p70 S6 kinase (Thr389) (Cell Signaling), anti-p62 (Progen) and anti-tubulin (Millipore) as the probes. After hybridizations, the blots were incubated at room temperature with the appropriate secondary antibodies and Western Lightning Plus-ECL (PerkinElmer). For quantitative analysis, the relative intensities of the bands were normalized against that of tubulin and expressed as means±SEM.

For analysis of insoluble proteins, the tissues were dissected and sequentially extracted with buffers of increasing strengths as previously described (K. J. Tsai et al. (2010) *J.*

Exp. Med. 207, 1661; M. Neumann et al. (2006) "Ubiquitinated TDP-43 in frontotemporal lobar degeneration and amyotrophic lateral sclerosis" Science 314, 130). In brief, the forebrains were extracted sequentially at 5 ml/g (volume/weight) with the low-salt (LS) buffer (10 mM Tris, pH 7.5, 5 mM EDTA, 1 mM DTT, 10% sucrose, and a cock- tail of protease inhibitors), high-salt Triton X-100 (TX) buffer (LS+ 1% Triton X-100+0.5 M NaCl), myelin floatation buffer (TX buffer containing 30% sucrose), and Sarkosyl (SARK) buffer (LS+1% N-Lauroyl-sarcosine+0.5 M NaCl). The SARK-insoluble materials were further extracted in 0.25 ml/g urea buffer (7 M urea, 2 M thiourea, 4% 3-[(3-Cholamidopropyl) dimethylammonio]-1-propanesulfonate, 30 mM Tris, pH 8.5). The urea soluble proteins were then analyzed by Western blotting.

Statistical Analysis.

All data are reported as the mean±S.E.M. Independent experiments were compared with each other by One-way ANOVA. Differences were considered statistically significant at $p<0.05$, as indicated by the asterisks.

Results

To test whether rapamycin could be used as an effective therapeutic drug for neurodegenerative diseases with TDP-43 proteinopathies, a FTLD-U mouse model was used for medical experimentation. These FTLD-U mice carried a TDP-43 transgene specifically overexpressed in the forebrain under the control of the CamKII promoter. At 2-month of age, they started to exhibit cognition impairment, and motor dysfunction became apparent at the age of 6 months. Various molecular and cellular abnormalities also developed along with the behavioral phenotypes which included down-regulation of several markers of the neuronal plasticity, neuronal loss, hippocampal atrophy, etc. Most significantly, TDP-43 proteinopathies became obvious at 6-month of age, with the appearance of poly-ubiquinated TDP-43 and the 35 KD, 25 KD fragments in the urea-soluble fractions of the cellular extracts of the forebrain.

For drug treatment, the FTLD-U mice were injected with rapamycin (10 mg/kg) or vehicle three times a week for a period of four months from the age of two months. During the treatment, the mice were subjected to the Morris water maze test at the age of 3 months and to rotarod test at the age of 6 months (FIG. 1A). As shown in FIG. 1B, the escape latency of TDP-43 Tg mice treated with rapamycin for 1 month was significantly shorter than the vehicle-treated Tg mice. The TDP-43 Tg mice were severely impaired in the motor coordination, balance and grip strength at the age of six months. However, the rotarod performance of the rapamycin-treated TDP-43 Tg mice were significantly better in comparison to the vehicle-treated Tg mice (FIG. 1C). The data in FIG. 1 indicated that rapamycin injection could rescue the impairment of learning/memory capabilities of the TDP-43 Tg mice and it also significantly prevented the age-dependent progressive loss of their motor function.

Figure 2A:
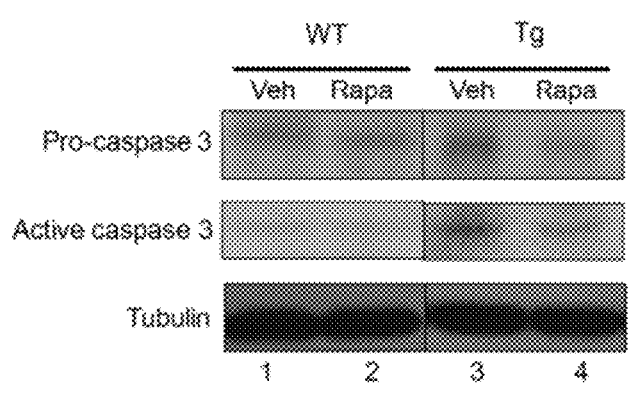
FIGS. 2A-H show rapamycin effects on the caspase-3 expression level and neuronal survival in the FTLD-U mouse brains. (2A-B) Western blotting analysis of the levels of pro- and active forms of caspase-3 in the extracts of isolated cortex and hippocampus from 6 month-old WT and TDP-43 Tg mice treated with rapamycin or vehicle. The blotting patterns are shown on the left (2A) and the statistical analysis is shown on the right (2B). *, $p<0.05$. (2C-E) Immunohistostaining of the active caspase-3 (upper 2 panels; 2C) in brain sections of TDP-43 Tg mice treated with rapamycin (Rapa) or vehicle (Veh) for 6 months. The quantitative analysis by tissue cytometry using the TissueQuest software is shown in the middle panels (2D) and the bottom histogram (2E). (2F-H) Immunohistostaining of NeuN(+) cells in the brain sections of TDP-43 Tg mice treated with rapamycin or vehicle for 6 months (the upper 2 panels; 2F). The quantitative analysis is shown in the middle 2 panels (2G) and the bottom histogram (2H). *, $p<0.05$.
Figure 2B:
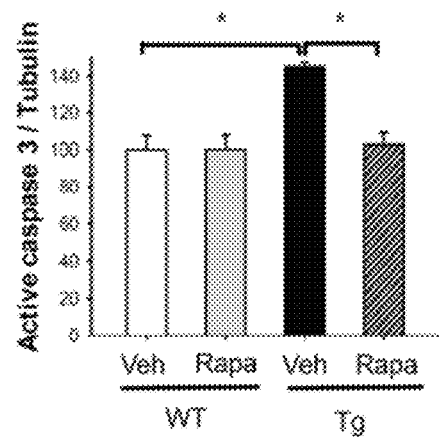
Figure 2C:
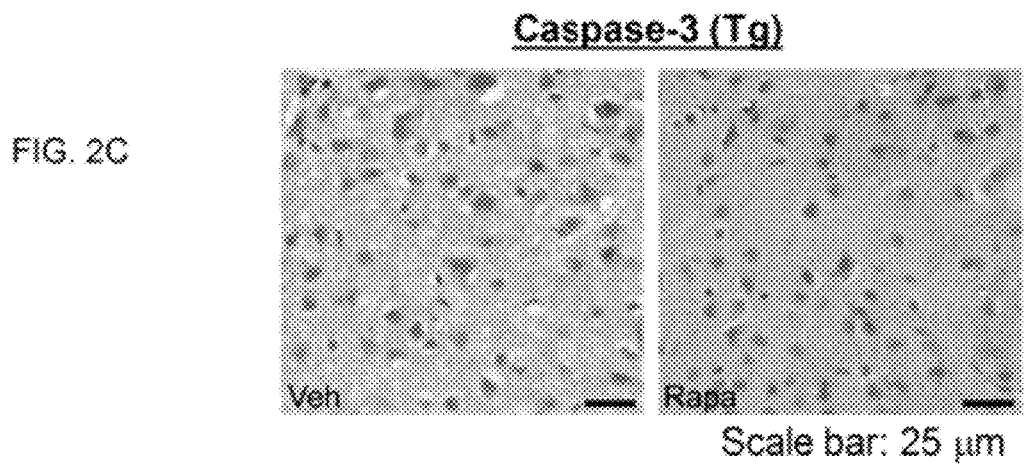
Figure 2D:
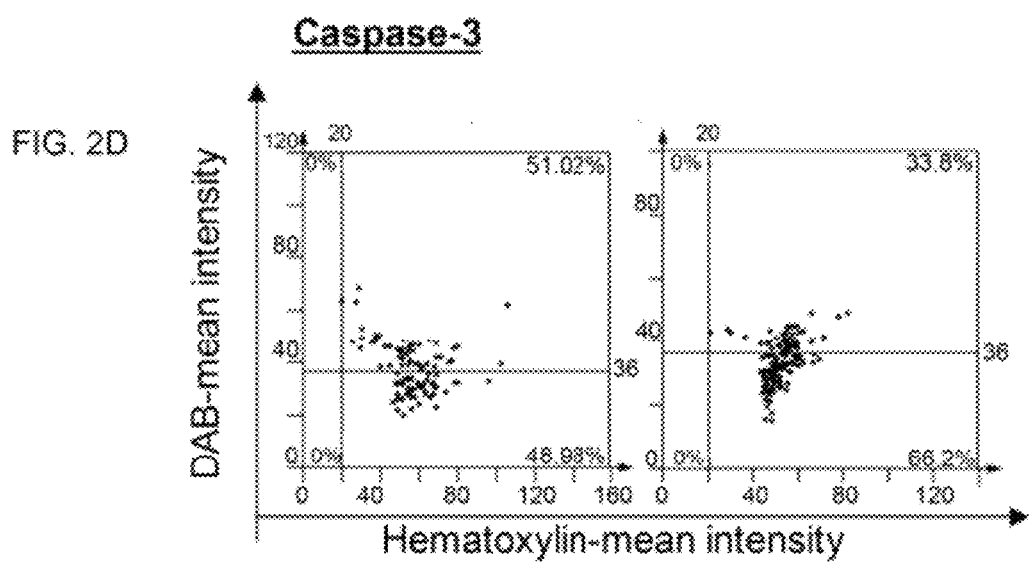
Figure 2E:
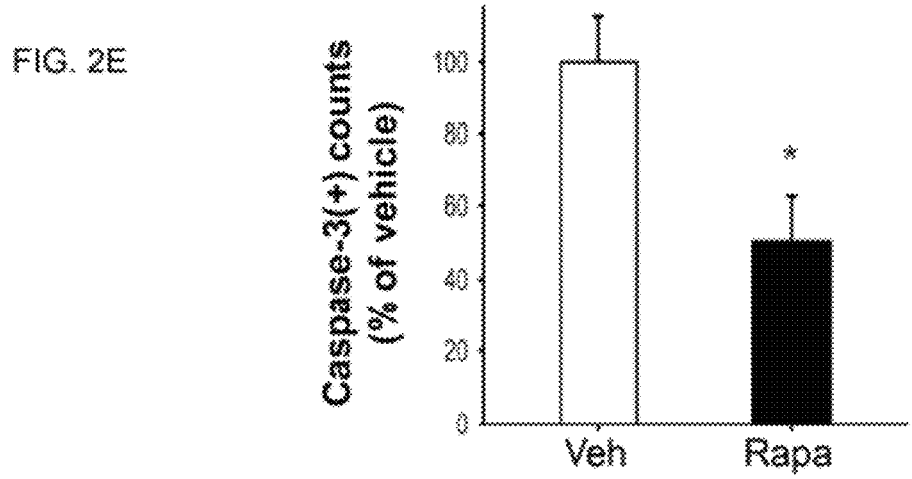
Figure 2F:
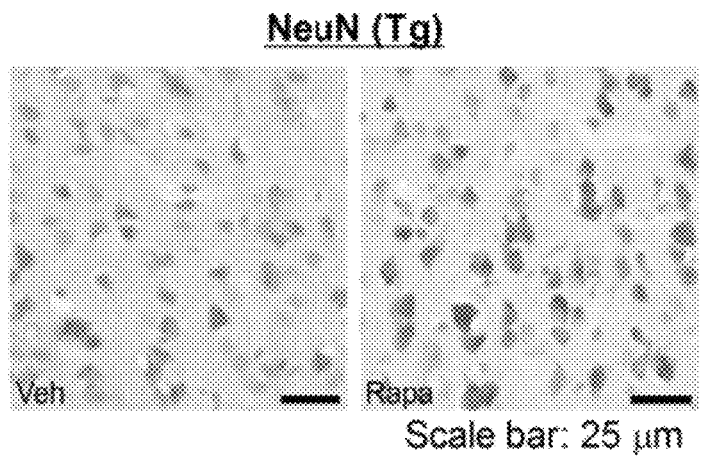
Figure 2G:
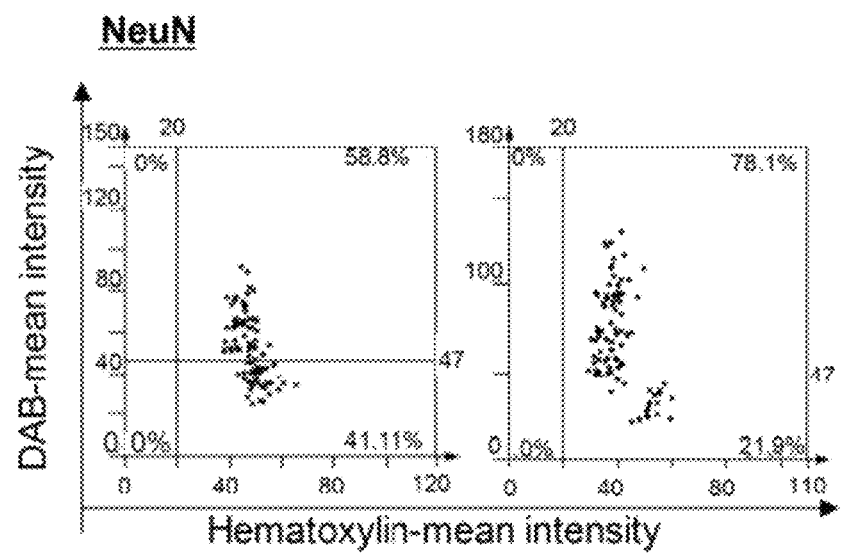
Figure 2H:
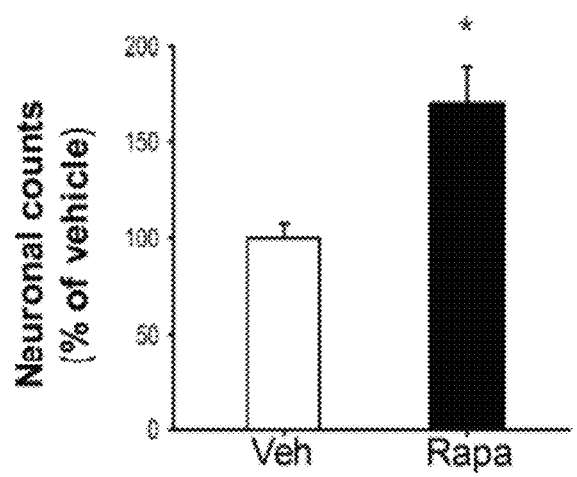

The TDP-43 Tg mice exhibited a caspase-3-dependent neuronal apoptosis at the age of 2 months. To determine whether the improvement of the spatial learning/memory capability of the 3 month-old TDP-43 Tg mice upon rapamycin treatment was due to, at least in part, the reduction in neuronal apoptosis, the expression levels of both the pro-caspase-3 and active caspase-3 were examined by Western blot analysis (FIGS. 2A-B). The result showed that the amounts of both the pro- and the active forms of caspase-3 were increased in the TDP-43 Tg mouse brains when compared to the WT mice (compare lanes 1 and 3, FIGS. 2A-B). After rapamycin treatment, the levels of both pro- and active forms of caspase-3 in the TDP-43 Tg mice (compare lanes 3 and 4, FIGS. 2A-B), but not the WT mice (compare lanes 1 and 2, FIGS. 2A-B), were significantly decreased. The decrease of the active caspase-3 in the rapamycin-treated TDP-43 Tg mice brain was confirmed by immunostaining analysis of the brain sections (FIGS. 2C, 2E). Significantly, the decrease of the caspase-3 levels after rapamycin treatment was coupled with an increase of the neurons (FIGS. 2F, 2H). The data of FIG. 2 altogether indicated that rapamycin treatment could reduce the neuronal apoptosis in the FTLD-U mice via modulation of the caspase-3-dependent pathway.

Whether the rapamycin treatment had any effect on the mis-metabolism of TDP-43 in the forebrain of the FTLD-U mice was also examined. Both cytosolic TDP-43 (+) UBIs and relatively insoluble forms of TDP-43, including the poly-ubiquitinated TDP-43 and the 35 KD/25 KD TDP-43 fragments, accumulated in the forebrains of 6 month-old FTLD-U mice. As shown first by Western blotting analysis, rapamycin treatment did not reduce the amounts of the full-length TDP-43 and the 35 KD/25 KD fragments in the soluble (RIPA) fraction of the total extracts from the cortex and hippocampus of 6 month-old FTLD-U mice (FIGS. 3A-D). On the other hand, the expression levels of the full-length TDP-43, poly-ubiquitinated TDP-43 (***) and the 35 fragment, the latter two of which were mainly detectable in the urea-soluble fraction of the forebrain extract, were all downregulated after 4 months of rapamycin treatment (FIG. 3E). This data suggested that rapamycin treatment might also inhibit the process of aggregate formation of mis-metabolized TDP-43 species. Indeed, as shown by immunohistochemistry and hematoxylin staining of the brain sections, the number of forebrain cells with cytosolic TDP-43 (+) inclusions and TDP-43 depleted nuclei in the 6-month-old FTLD-U mice was greatly reduced after treatment with rapamycin (FIGS. 3F-G). Overall, the data of FIG. 3 indicated that rapamycin treatment inhibited the formation of TDP-43 (+) inclusions in the diseased cells of the FTLD-U mouse brains, likely due to its capacity of enhancing the autophagic clearance which would degrade the abnormally generated TDP-43 species before their aggregation in the cytosol.

Figure 4A:
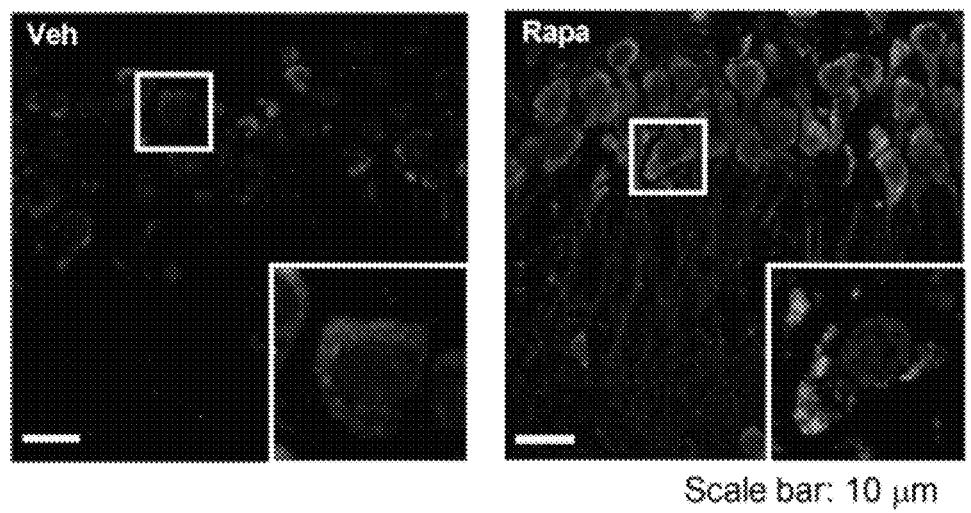
FIGS. 4A-E show effects of rapamycin treatment on autophagy in the forebrains of WT and TDP-43 Tg mice. (4A) Representative immunofluorescent images of the hippocampus of TDP-43 Tg mice treated with rapamycin/vehicle after staining with anti-LC3 (green) and DAPI (blue). Note the increase of the LC3 puncta in the rapamycin-treated Tg mouse sample in comparison to the vehicle-treated one. Bars, 10 μm. (4B-E) Western blot analysis of the expression levels of LC3, p62, and P-p70. The levels of the proteins and the tubulin control in the extracts of the isolated cortex and hippocampus from WT and TDP-43 Tg mice with or without rapamycin treatment were measured by Western blotting. (4B) The blot patterns. The comparisons among the WT and Tg mice treated with rapamycin (Rapa) or vehicle (Veh) are shown in the histogram for LC3-II and LC-3(4C), p62(4D), and P-p70(4E), respectively. For all three histograms, the protein levels are first normalized against that of the tubulin and then compared relative to the WT (Veh) samples.
Figure 4B:
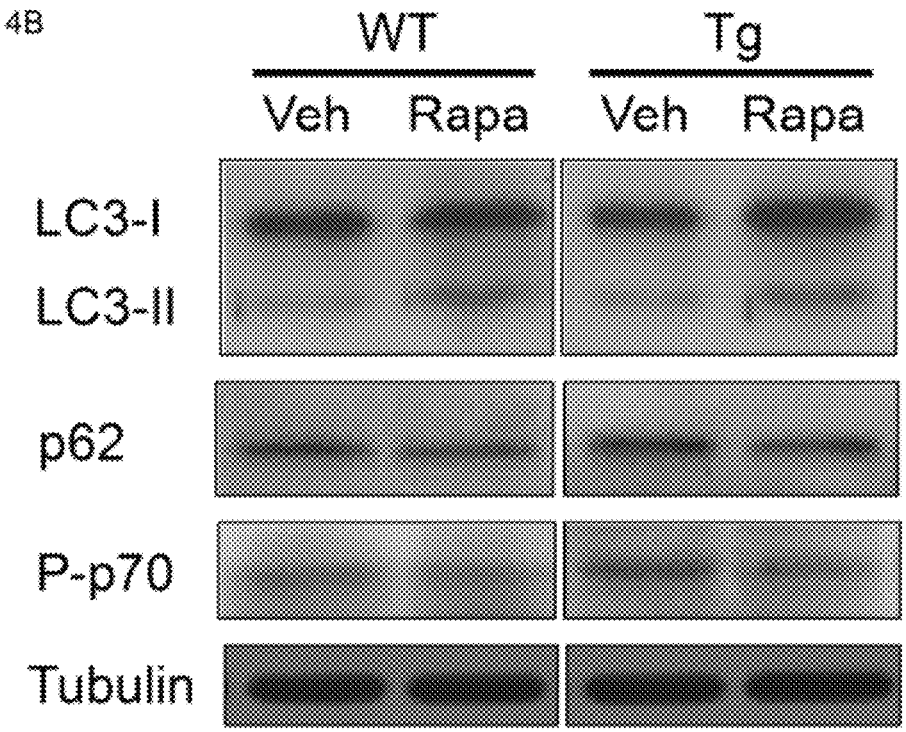
Figure 4C:
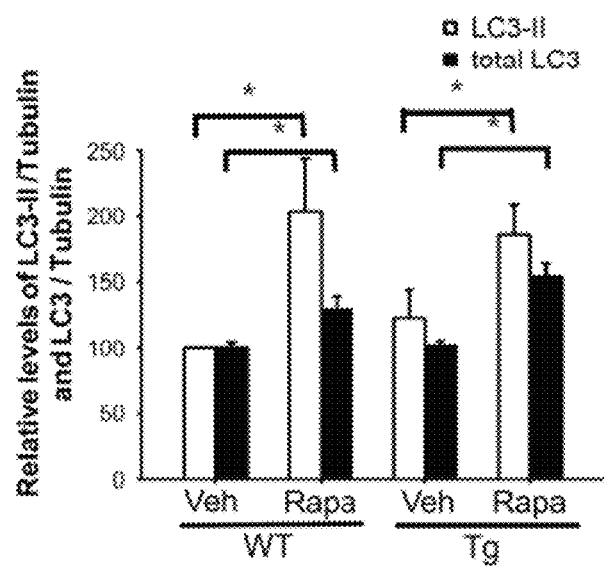
Figure 4D:
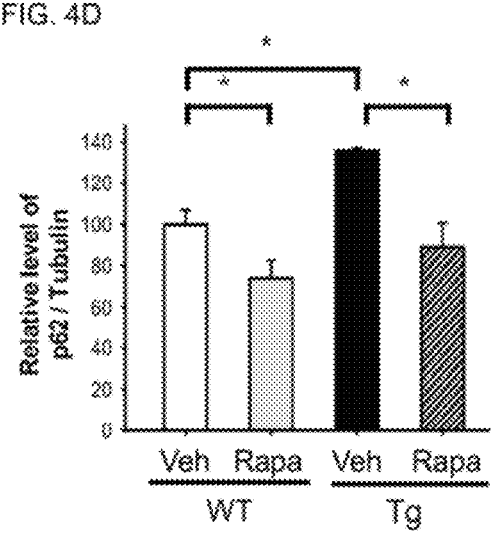
Figure 4E:
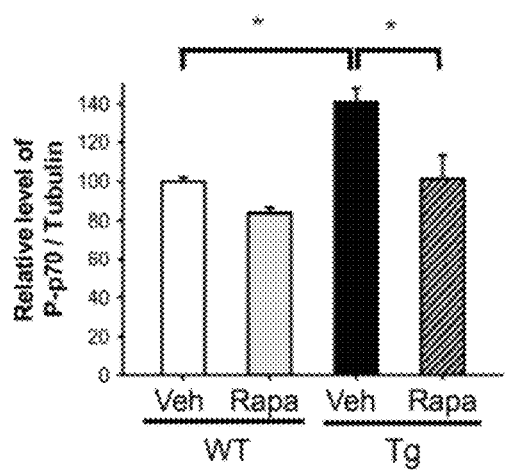

To investigate whether the abolishment of the TDP-43 (+) inclusions in the forebrains of the FTLD-U mice by the rapamycin treatment was coupled with the mTOR-regulated autophagy process, the levels of several autophagic and mTOR activity markers were examined by immunofluorescence staining and/or Western blotting. As shown in FIG. 4A, the autophagosome marker LC3-positive puncta, which represented the presence of the autolysosomes, were significantly elevated in the cortex region of rapamycin-treated FTLD-U mice when compared to the vehicle-treated ones (FIG. 4A). During the autophagosome formation, LC3-I is processed to LC3-II by lipidation. Thus, the level of LC3-II would increase during the synthesis of the autophagosome. Consistent with the observation in FIG. 4A, it was found that the ratios of both LC3-II/tubulin and LC3/tubulin in the cortex and hippocampus regions of rapamycin-treated FTLD-U as well as WT mice were significantly increased when compared to the vehicle-treated mice (FIGS. 4B-C), indicating that rapamycin enhanced the autophagosome formation and also triggered the latter steps of the autolysosome formation during the autophagy process. Interestingly, the level of p62/SQSTM1, an autophagic flux marker down-regulated along the autophagy pathway (S. Pankiv et al. (2007) "p62/SQSTM 1 binds directly to Atg8/LC3 to facilitate degradation of ubiquitinated protein aggregates by autophagy" J. Biol. Chem. 282, 24131), in the vehicle-treated FTLD-U mouse brain was higher than that of the vehicle-treated WT mouse brain, indicating an incomplete autophagy in the mouse brain upon over-expression of TDP-43 (FIGS. 4B and 4D). Upon rapamycin treatment, however, the levels of p62 in the forebrains of both the FTLD-U and WT mice were reduced (FIGS. 4B and 4D), suggesting the enhancement of autophagy in the WT mouse brain and rescue of the autophagy in the FTLD-U mouse brain, respectively. The above observations were indeed the results of inhibition of the mTOR signaling pathway by rapamycin, as reflected by the reductions of the levels of the phospho-p70 S6 kinase (P-p70) in the hippocampus regions of the brains of rapamycin-treated FTLD-U as well as WT mice in comparison to the vehicle-treated mice (FIGS. 4B and 4E).

The above study has shown that mTOR inhibition by rapamycin could recover the learning/memory capability and prevent the loss of motor neuron function of the TDP-43 Tg mice with pathological phenotypes of FTLD-U. Furthermore, the phenotypic recoveries are accompanied with the clearance of the TDP-43 (+) UBIs in the FTLD-U mouse brains through autophagy. In great contrast, however, it has been found that rapamycin treatment could not rescue the phenotype of an ASL mouse model with transgenic overexpression of the mutant SOD1G93A protein (X. Zhang et al. (2011) "Rapamycin treatment augments motor neuron degeneration in SOD1(G93A) mouse model of amyotrophic lateral sclerosis" *Autophagy* 7, 412).

In the case of our FTLD-U mice, the rapamycin treatment reduces the amounts of insoluble TDP-43 species (FIG. 3B) as well as the formation of the TDP-43 (+) inclusions (FIG. 3C) in the forebrain region of the TDP-43 Tg mice. This was accompanied with a recovery of the autophagy as indicated by the analysis of different autophagy markers (FIG. 4). However, the levels of the soluble non-aggregate forms of the different TDP-43 species were not affected by the rapamycin treatment. Our data provides the first in vivo evidence that rapamycin-induced autophagy could play an active role in the clearance of TDP-43 aggregates and in the reduction of inclusion formation, possibly in part through binding of the inclusions with p62/SQSTM1 and subsequent autophagic degradation.

Figure 5:
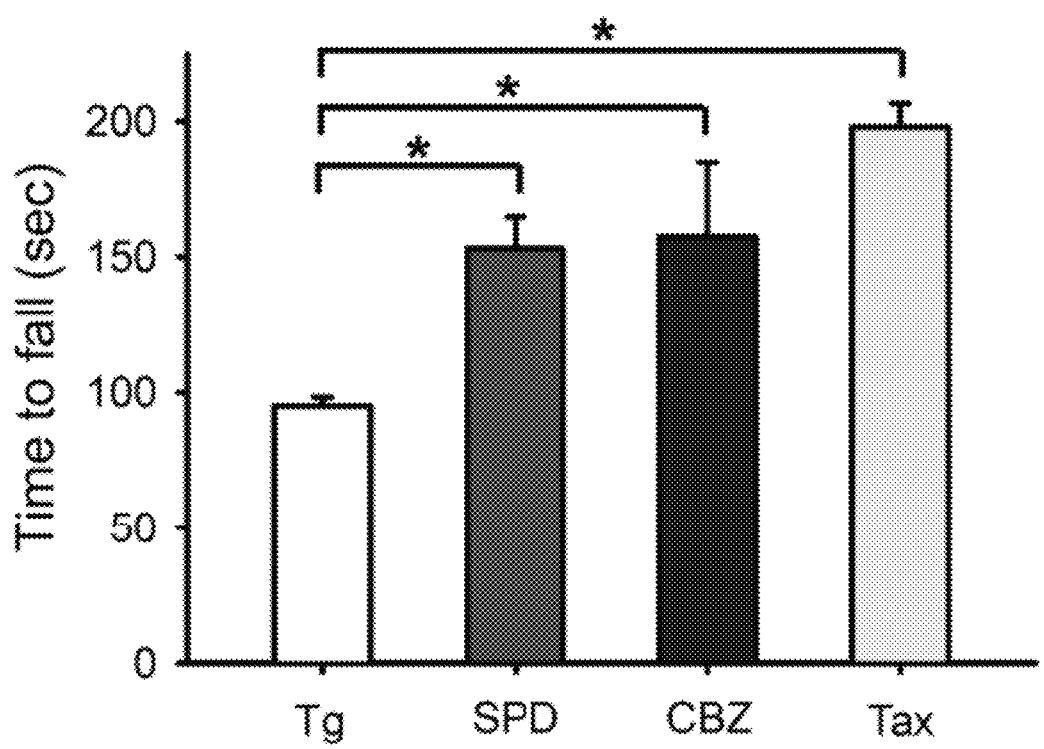
FIG. 5 shows the effects of spermidine, carbamazepine and tamoxifen, in rescuing the motor function deficits of the FTLD-U mice.

FIG. 5 shows three other autophage inducers, spermidine, carbamazepine and tamoxifen, rescued the motor function deficits of the FTLD-U mice.

In summary, it was demonstrated that rapamycin is an effective drug for therapy of an animal with FTLD-U phenotypes. The elevation of the LC3/LC3-II and reduction of p62 upon rapamycin treatment indicate that the cells in the forebrain of the mice, despite of overexpression of TDP-43 and formation of the TDP-43 (+) inclusions, still maintain an autophagy system, albeit impaired, that are responsive to and reusable by pharmacological stimuli. The study thus has set the basis for future therapy of neurodegenerative diseases with TDP-43 proteinopathies by pharmacologically targeting the autophagy.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of alleviating and/or rescuing a motor function deficit associated with frontotemporal lobar degeneration with ubiquitinated inclusions (FTLD-U) comprising:
    administering to an animal in need of alleviating and/or rescuing the motor function deficit associated with frontotemporal lobar degeneration with ubiquitinated inclusions (FTLD-U) a therapeutically effective amount of rapamycin, and thereby alleviating and/or rescuing the motor function deficit associated with the FTULD-U, wherein the animal has an early stage of frontotemporal lobar degeneration without exhibiting ubiquitinated inclusions in the forebrain thereof.

2. The method. of claim 1, further comprising:
    evaluating the motor coordination and/or balance of the animal.

3. A method of decreasing and/or alleviating the presence of ubiquitinated TDP-43, comprising:
    administering to an animal in need of decreasing and/or alleviating the presence of ubiquitinated TDP-43a therapeutically effective amount of rapamycin, and thereby decreasing and/or alleviating the presence of ubiquitinated TDP-43, wherein the animal has an early stage of frontotemporal lobar degeneration without exhibiting ubiquitinated inclusions in the forebrain thereof.

4. The method of claim 3, wherein the animal suffers from learning and/or memory impairment.

5. The method of claim 3, further comprising:
    evaluating the motor coordination and/or balance of the animal.

6. A method of alleviating and/or rescuing learning, memory and motor function deficits associated with frontotemporal lobar degeneration with ubiquitinated inclusions (FTLD-U), comprising:
    administering to an animal in need of alleviating and/or rescuing the learning, memory and motor function deficits associated with frontotemporal lobar degeneration with ubiquitinated inclusions (FTLD-U) a therapeutically effective amount of all autophagy inducer; and
    thereby alleviating and/or rescuing the learning, memory and motor function deficits associated with FTLD-U, wherein the animal has an early stage of frontotemporal lobar degeneration exhibiting the memory and/or learning deficits but without exhibiting ubiquitinated inclusions in the forebrain thereof wherein the autophagy inducer is at least one chosen from rapamycin, tamoxifen, carbamazepine, calpastatin, minoxidil, spermidine, and trehalose.

7. The method of claim 6, further comprising:
    assessing the leanrning and/or memory capacities of the animal; and/or evaluating the motor coordination and/or balance of the animal.

* * * * *